(12) United States Patent
Isozaki et al.

(10) Patent No.: US 7,394,532 B2
(45) Date of Patent: Jul. 1, 2008

(54) SURFACE INSPECTION METHOD AND APPARATUS

(75) Inventors: Hisashi Isozaki, Tokyo (JP); Michihiro Yamazaki, Tokyo (JP); Hiroshi Yoshikawa, Tokyo (JP); Takehiro Takase, Tokyo (JP); Yutaka Shida, Tokyo (JP); Yoichiro Iwa, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 356 days.

(21) Appl. No.: 10/680,432

(22) Filed: Oct. 8, 2003

(65) Prior Publication Data
US 2004/0130727 A1 Jul. 8, 2004

(30) Foreign Application Priority Data
Oct. 9, 2002 (JP) ............................. 2002-295613

(51) Int. Cl.
*G01N 21/00* (2006.01)
*G01B 11/28* (2006.01)
(52) U.S. Cl. ...................................... 356/237.2; 356/630
(58) Field of Classification Search ... 356/237.1–237.5, 356/239.1, 394, 364–369, 630–632
See application file for complete search history.

(56) References Cited

U.S. PATENT DOCUMENTS

| | | | | |
|---|---|---|---|---|
| 4,966,457 A | | 10/1990 | Hayano et al. | |
| 5,179,422 A | * | 1/1993 | Peterson | 356/237.1 |
| 5,381,233 A | * | 1/1995 | Chao et al. | 356/369 |
| 5,548,404 A | * | 8/1996 | Kupershmidt et al. | 356/368 |
| 6,104,481 A | * | 8/2000 | Sekine et al. | 356/237.5 |
| 6,115,117 A | * | 9/2000 | Isozaki | 356/237.4 |
| 6,554,111 B2 | * | 4/2003 | Schaefer et al. | 188/352 |
| 6,587,192 B2 | * | 7/2003 | Isozaki et al. | 356/237.2 |
| 6,771,364 B2 | * | 8/2004 | Isozaki et al. | 356/237.2 |
| 6,847,444 B2 | * | 1/2005 | Isozaki et al. | 356/237.3 |
| 6,943,876 B2 | * | 9/2005 | Yoshida et al. | 356/237.2 |
| 2002/0021438 A1 | * | 2/2002 | Isozaki et al. | 356/237.5 |
| 2003/0184744 A1 | * | 10/2003 | Isozaki et al. | 356/237.2 |
| 2004/0119971 A1 | * | 6/2004 | Isozaki et al. | 356/237.2 |

FOREIGN PATENT DOCUMENTS

| | | |
|---|---|---|
| CN | 2001-0072848 | 7/2001 |
| EP | 0 291 276 B1 | 8/1993 |
| JP | 11-064235 | 3/1999 |
| JP | 2001-281162 A | 10/2001 |
| WO | WO 00/12958 | 3/2000 |

\* cited by examiner

*Primary Examiner*—Hoa Q Pham
(74) *Attorney, Agent, or Firm*—Foley & Lardner LLP

(57) ABSTRACT

A method and an apparatus of inspecting the surface of a wafer, where two or more kinds of laser are switched or mixed to make the laser incident on the film-coated wafer by a same incident angle, in which inspection data regarding an inspection apparatus and film parameters regarding a film are stored in storage means of the inspection apparatus in an associated state with each other so as to obtain predetermined inspection conditions. When performing each measurement, an operator sets the film parameters of the wafer to be measured by setting means of the inspection apparatus. Thus, desired inspection conditions are automatically set in the inspection apparatus. The film parameters that the operator sets at each measurement are a film thickness and a film refraction index.

11 Claims, 7 Drawing Sheets

FILM THICKNESS AND REFLECTANCE
WHEN 3 WAVELENGTHS ARE USED    SiO2

SURFACE INSPECTION METHOD AND APPARATUS

BACKGROUND OF THE INVENTION

1. Field of the Invention

The present invention relates to a surface inspection method and an apparatus to inspect a film-coated inspection subject such as a wafer. For example, the present invention relates to a surface inspection method and an apparatus to inspect foreign particles or flaws, which exist on the surface of a semiconductor wafer having a film structure, by two or more kinds of laser.

2. Related Art

By inspecting the surface of a wafer for inspection, it is possible to indirectly control the status of manufacturing equipment that processed the wafer.

Conventionally, when inspecting the surface of a filmless wafer, it has been unnecessary to take the quality of the wafer itself into consideration because the reflectance at the wafer surface is substantially fixed.

For this reason, a calibration wafer, where reference grains whose grain diameter is known are coated on its surface by a predetermined number, is commonly used for each of different measurement to perform calibration, and thus it was possible to control accuracy.

Therefore, it is understood that the calibration by the calibration wafer has been used for controlling an inspection apparatus itself.

On the other hand, when a film-coated wafer is used as an inspection subject, an operator sequentially sets the inspection conditions or the like of the surface inspection apparatus for each wafer to be inspected so as to combine the conditions with the value of each parameter regarding the film on the wafer. Thus, the operator has set an optimum calibration curve used in the inspection.

Optical conditions such as surface reflectance, film refraction index, internal reflection, and the like vary due to the thickness and the quality of the film formed on the wafer. For this reason, it is required to stabilize inspection sensitivity taking the thickness and quality of the wafer itself, which is a measurement subject, in consideration. So, it is usually the case that the operator stabilizes the sensitivity by changing the condition settings regarding the wafer to be inspected for each measurement. Refer to the description of the prior art written in Japanese Patent Laid-Open No. 2001-281162.

For example, in the case of a wafer having a particular film structure such as a SOI wafer that has been used in recent years, the status of each wafer itself is strictly inspected. To set the optimum inspection sensitivity, light quantity and polarization are set as inspection data. At this point, the operator has manually set desired optical inspection conditions taking the interrelationship between the inspection data and film parameters (film type, film number, refraction index and the like) in thorough consideration. Such condition settings have been complicated and difficult for the operator and advanced knowledge and experience have been required.

As described, to perform the optimum surface inspection for the film-coated wafer, it has been necessary for the operator to properly set the conditions for each measurement while associating the film parameters (such as film thickness and refraction index) regarding the film on the wafer to be inspected with corresponding inspection data (such as wavelength of inspection light, polarization status, incident angle on wafer surface) of the inspection apparatus, in other words, with an optimum correlation.

Conventionally, the operator has manually entered to set the inspection data such as the wavelength of inspection light, polarization status and incident angle for each measurement based on the film parameters (film thickness and refraction index in particular) of the wafer to be inspected on the basis of a known mutual correlation.

For example, the operator has described the values of each film parameter in the form of a comma-delimited text format data and had the inspection apparatus read the value.

However, such a condition settings operation by the operator is a complicated and difficult operation where he/she selects the optimum optical inspection conditions and sets the values while taking a plurality of film parameters in consideration. Only an experienced operator can properly execute the operation. Additionally, the operation has overloaded even the experienced operator.

Further, in the surface inspection apparatus, when it is impossible to switch (or mix) the wavelengths on one apparatus and one incident angle, it has been difficult to set the inspection conditions of the inspection apparatus to the optimum conditions with respect to the film thickness and film refraction index of the wafer to be inspected.

Furthermore, when changing the configuration or the settings of the apparatus, it has been impossible to automate the settings for the wavelength of the inspection light and the polarization of incident angle corresponding to the film thickness and film refraction index of the wafer to be inspected.

SUMMARY OF THE INVENTION

The object of the present invention is to provide the surface inspection method and apparatus, by which even a non-experienced operator can set the optimum inspection conditions simply and easily.

Preferable modes of the present invention are exemplified as follows.

(1) A method of inspecting the surface of an inspection subject, where two or more kinds of laser are switched or mixed to make them incident on the film-coated inspection subject by a same incident angle, in which the inspection data regarding the inspection apparatus and the film parameters regarding the film on the inspection subject are previously associated with each other and stored in the inspection apparatus so as to obtain predetermined optical inspection conditions, the operator sets the film parameters of the inspection subject to be measured to the inspection apparatus, and thus automatically setting predetermined inspection conditions in the inspection apparatus.

(2) An apparatus for inspecting the surface of an inspection subject, where two or more kinds of laser are switched or mixed to make them incident on the film-coated inspection subject by a same incident angle, which comprises storage means for storing the inspection data regarding the inspection apparatus and the film parameters regarding the film on the inspection subject by associating with each other so as to obtain the predetermined optical inspection conditions, parameter setting means for setting by the operator the film parameters of the wafer to be measured in performing measurement, arithmetic means for automatically calculating the predetermined inspection conditions based on the parameters set by the parameter setting means, and control means for controlling each section of the apparatus based on the predetermined inspection conditions calculated by the arithmetic means.

The present invention is capable of automatically setting the optimum optical inspection conditions from the film parameters entered for each measurement by the operator based on the optimum correlation between the inspection data of the inspection apparatus and the parameters of the film attached to the inspection subject (wafer, for example). For example, the parameters (such as film number, film type, film thickness and the like in the case of film-coated wafer) that is made clear on the manufacturing process of the inspection subject to be inspected and the inspection data are associated and previously stored, and the optimum optical inspection conditions can be automatically set from the film parameters entered for each measurement by the operator.

The present invention is an improved method and apparatus, which inspect a wafer surface, by making laser having two or more wavelengths incident on the film-coated wafer in a switched or mixed manner by a same incident angle. The inspection data regarding the inspection apparatus are previously associated with the film parameters regarding the film with each other so as to obtain the predetermined optical inspection conditions, in other words, with an optimum correlation, and they are stored in the storage means of the inspection apparatus. In performing each measurement, the operator sets the film parameters of the wafer to be measured by the setting means of the inspection apparatus. Thus, the desired optical inspection conditions are automatically set in the inspection apparatus. The film parameters that the operator sets for each measurement are the film thickness and the film refraction index.

Firstly, description will be made for primary constituents that constitute the surface inspection apparatus according to the preferred embodiments of the present invention.

Light Source Section

The section emits a first luminous flux and a second luminous flux.

Irradiation Optical System

The system irradiates the first luminous flux and second luminous flux on the surface of the film-coated inspection subject.

Displacement Section

The section relatively displaces the film-coated inspection subject and the irradiation luminous flux of the irradiation optical system.

Light-Receiving Optical System

The system receives scattered light generated from the inspection subject on the surface of the film-coated inspection subject after irradiation of the first luminous flux from the irradiation optical system and scattered light generated from the inspection subject on the film-coated inspection subject after irradiation of the second luminous flux from the irradiation optical system.

First Light-Receiving Section

The section transforms the scattered light of the first luminous flux received by the light-receiving optical system into a first light reception signal.

Second Light-Receiving Section

The section transforms the scattered light of the second luminous flux received by the light-receiving optical system into a second light reception signal.

Storage Means

The inspection data (data regarding wavelength of inspection light, polarization, incident angle and the like) of the inspection apparatus are associated with various kinds of parameters (such as film thickness and refraction index) regarding the film so as to have the optimum correlation, and previously stored in the storage means.

Control Arithmetic Means

The means has the arithmetic means, the control means and the like.

Arithmetic Means

The arithmetic means automatically calculates (selects) the values for the proper optical inspection conditions based on the film parameters input to the apparatus in performing measurement according to the correlation between the inspection data and the film parameters stored in the storage means.

Control Means

The means controls the wavelength of the inspection light, polarization, incident angle and the like based mainly on the data from the arithmetic means.

Interface Means

The means displays information for the operator and enables the operator to enter desired data. The interface means includes display means and setting means (monitor, keyboard, mouse, touch panel and the like, for example).

Sensor Means

The means detects (monitors) the wavelength of the inspection light, polarization and incident angle.

The present invention comprises the above-described constituents and so on, and inspects the surface of each wafer focusing attention particularly on the thickness and the refraction index of the film on the wafer. This is because the variation of the detection sensitivity largely depends on the variation of the thickness and reflectance of the film formed on the wafer when the wafer having the film structure on its surface is the inspection subject.

Generally, the variation of reflectance is mainly caused by the film thickness, incident angle, wavelength and polarization. When the incident angle, wavelength and polarization are determined for the film thickness of the wafer to be measured, the optimum optical inspection conditions are derived from the wafer to be measured.

The refraction index corresponding to the wavelength of the film formed on the wafer to be inspected is previously stored as the film parameter (including the correlation with the film thickness) in the storage means of the inspection apparatus, the operator enters (selects) only the film thickness of the wafer to be measured when performing each measurement, and thus finding the optimum optical inspection conditions based on the stored refraction index. Accordingly, the optimum inspection conditions are set to the inspection apparatus very easily. As a result, it is possible to detect the foreign particles on the film-coated wafer to be measured with good sensitivity, and extremely efficient measurement can be performed.

Regarding the value of film thickness, since the film thickness is an item that is constantly controlled on the manufacturing process of wafers, it is possible to obtain the value specifically, which is accurately measured by a thicknessmeter, as a known one for each wafer.

Preferably, the interface means, particularly its display section, of the surface inspection apparatus provides a data input screen for inputting the film parameters.

Other than the film thickness and refraction index, the followings can be preferably added as the film parameters.

(1) Film number (multiple layer film, single film)

(2) Film thickness and dispersion of each layer (such as input of %)

(3) Refraction index by the wavelength of each layer

Material of Each Layer
(4) Wafer name (inspection conditions stored for each wafer)

The inspection apparatus automatically calculates (selects) the optimum optical inspection conditions for the wavelength, incident angle, polarization and the like according to the optimum correlation previously stored corresponding to the film parameters that the operator enters in performing measurement.

The optimum inspection conditions may be individually prepared in accordance with each value of the film parameters, or the optimum inspection conditions may be found when the film parameters previously registered are called.

Note that, in the case where operator's determination is required or guidance is shown for the operator, it is preferable to display the calculation result by the arithmetic means and a graph of the reflectance and film thickness. At this point, it is possible to show a marker to the film thickness of the wafer for user-friendly display.

If the condition settings of the inspection data for the film parameters entered by the operator when performing each measurement are sufficient, the optimum optical inspection conditions are automatically selected and set.

When only the previously stored inspection data and film parameters are not sufficient, it is preferable a plurality of optimum inspection conditions and actually perform measurement, which makes it possible to determine one set of optimum inspection conditions. For example, in the case where a polarization component is taken in consideration, whether P-polarized light or S-polarized light is better is based empirically on the surface roughness of film in most cases. However, since the surface roughness also depends on the recipe of the apparatus that forms the film, which is difficult for the operator to know. Therefore, several optimum inspection conditions are prepared in advance, from which a user can easily select or enter actually suitable conditions. For this purpose, it is desirable to show a plurality of optimum conditions. In this case, it is preferable that the display screen of the interface means perform display to prompt the operator for a measurement operation. The operator can instruct the apparatus on the measurement operation after he/she knew the purpose from the display content on the screen. On the contrary, the operator may be able to deny the display content.

Further, it is preferable to make the screen be capable of performing display to prompt the operator for selecting the optical inspection conditions based on the inspection data previously stored.

Condition settings corresponding to the inspection subject, which are the foreign particles having a predetermined grain diameter or more, a shape with respect to a scanning direction, and the like, for example, can also be arbitrarily set according to various conditions and stored. If there are optimum ones in the inspection data and film parameters, which have already been entered, they are properly selected and shown for the operator, and can be set as the optimum optical inspection conditions.

Note that the surface inspection apparatus preferably comprises switching means of an optical path from the light source, changing means of the incident angle and polarization angle, a polarizer arranged in the optical path, and polarizer movable means capable of inserting/removing the polarizer in/from the optical path.

Note that the film structure includes a transmissive film in the specification. The film structure could be the transmissive film depending on the refraction index.

PREFERRED EMBODIMENTS OF THE INVENTION

Figure 1:
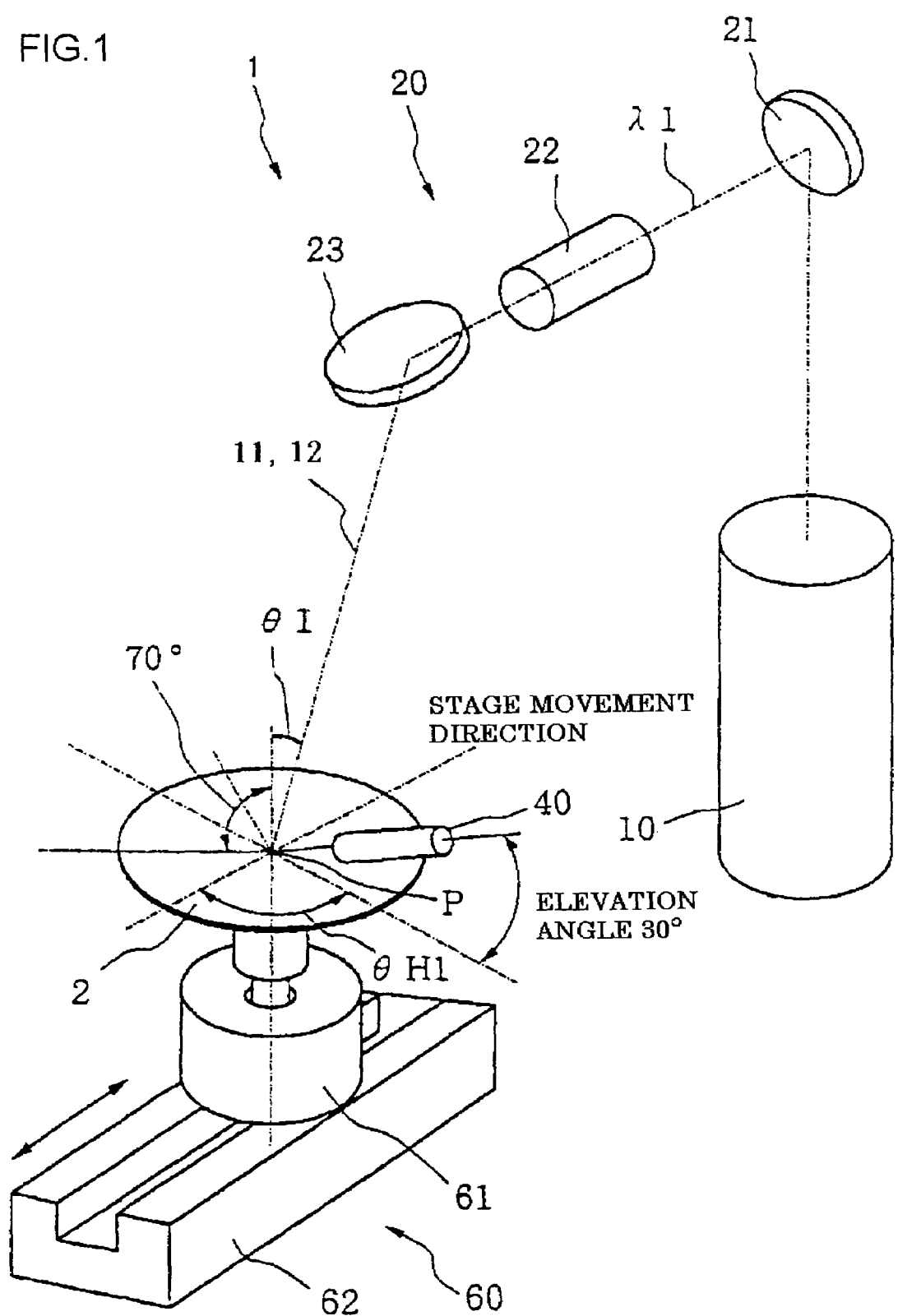
FIG. 1 is a schematic arrangement view of a primary optical component of a surface inspection apparatus according to one preferred embodiment of the present invention.
Figure 2:
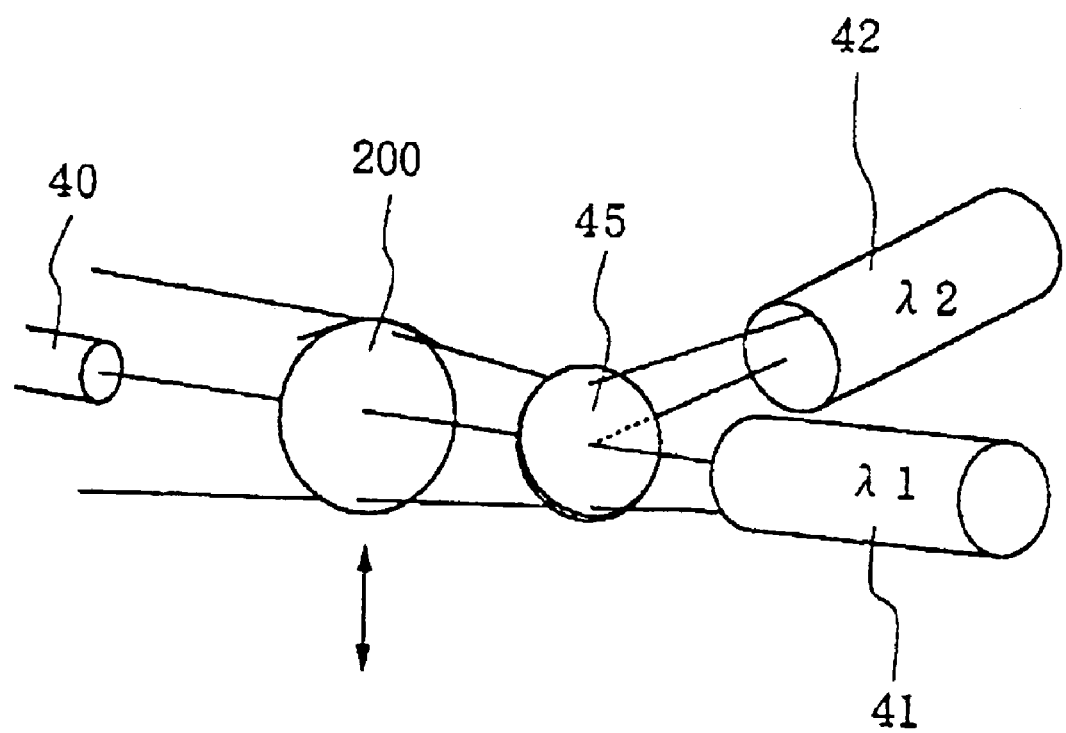
FIG. 2 is a detail view of a light-receiving optical system.
Figure 3:
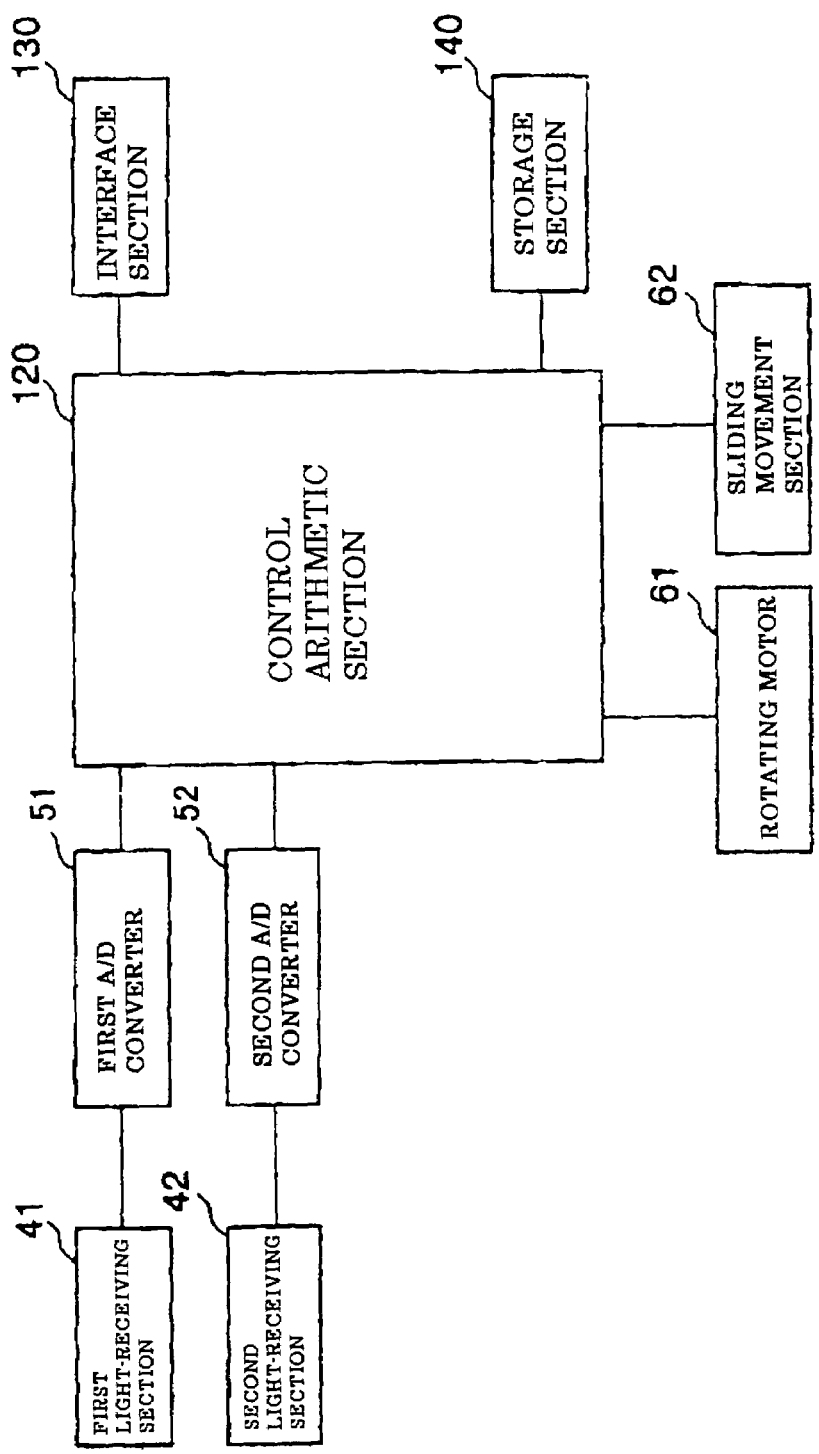
FIG. 3 is a block diagram of the surface inspection apparatus shown in FIG. 1.

FIGS. 1 to 3 are the schematic arrangement views of the primary component of the surface inspection apparatus according to one preferred embodiment of the present invention.

A surface inspection apparatus 1 has: a light source section 10 such as a laser tube that emits at least a luminous flux 11 having a first wavelength $\lambda 1$ and a luminous flux 12 having a second wavelength $\lambda 2$ different from $\lambda 1$; an irradiation optical system 20 that irradiates the luminous flux 11 having the first wavelength $\lambda 1$ and the luminous flux 12 having the second wavelength $\lambda 2$ on an inspection point P on the surface of a film-coated semiconductor wafer 2 as the film-coated inspection subject by a first irradiation angle $\theta 1$; a light-receiving optical system 40 that receives the scattered light from the inspection point P on the surface of the semiconductor wafer 2, which is caused by the luminous fluxes 11, 12 irradiated from the irradiation optical system 20, from a first light-receiving direction; and a displacement section 60 capable of moving the film-coated semiconductor wafer 2 as the film-coated inspection subject linearly and rotatably for the irradiation luminous flux 11 from the irradiation optical system 20 in a relative manner. The elevation angle of the light-receiving optical system 40 in FIG. 1 is 30°.

Description will be made for the light source section 10. The light source section 10 emits at least the luminous flux 11 having the first wavelength and the luminous flux 12 having the second wavelength different from the first wavelength. Various kinds of light source that emit luminous fluxes having different wavelengths can be used as the light source section 10. For example, a multi-line laser where one light source emits luminous fluxes having a plurality of wavelengths or one that synthesizes luminous fluxes from a plurality of light sources, which emit luminous fluxes having different wavelengths, with a half mirror to form one beam can be adopted.

When a luminous flux having an unnecessary wavelength occurs in the case of adopting the multi-line laser, the luminous fluxes are made to pass a band-pass filter that passes the first wavelength and the second wavelength, and thus only luminous fluxes having necessary wavelengths can be brought out.

When a plurality of light sources that emit luminous fluxes of different wavelengths are used, a plurality of the luminous fluxes are synthesized by the half mirror or the like to form one beam.

In the case of using an argon ion laser as the light source section 10 in the examples of FIGS. 1 to 3, the wavelength of 488 nm and the wavelength of 514.5 nm can be selected. The direction of the luminous flux 11 having the first wavelength and the luminous flux 12 having the second wavelength, which have been emitted from the light source 10, is changed by a first mirror 21, and the luminous fluxes are irradiated on the irradiation point P on the surface of the film-coated inspection subject 2 by the first irradiation angle θ1 via a first irradiation lens group 22 and a second mirror 23.

If the inspection subject, that is, the foreign particle or the like, exists on the inspection point P, the scattered light occurs according to a predetermined directivity when the irradiation luminous flux is irradiated on the subject. The first irradiation angle θ1 is set using a normal line direction of the film-coated inspection subject 2 as a reference.

In the embodiment of FIGS. 1 to 3, sizes of the first wavelength λ1 and the second wavelength λ2 can be arbitrarily selected.

Next, the light-receiving optical system 40 will be described. The light-receiving optical system 40 is provided to receive the above-described scattered light. The light-receiving optical system 40 receives the scattered light from the inspection point P on the surface of the film-coated semiconductor wafer 2, which is caused by the luminous fluxes 11, 12 irradiated from the irradiation optical system 20, from a first light-receiving direction. A first light-receiving horizontal angle θH1 (90° for example) in the first light-receiving direction is measured using a reflection direction of the irradiation luminous fluxes 11, 12 from the irradiation optical system 20, which is caused when the fluxes have made a specular reflection on the film-coated inspection subject 2, as a reference. A light-receiving elevation angle in the first light-receiving direction is set to 30°, for example.

As shown in FIG. 2, the luminous flux received by the light-receiving optical system 40 passes an ND filter 200 movably arranged in the arrow directions to be inserted in or withdrawn from a light reception optical path, and then is separated into the luminous flux having the first wavelength λ1 and the luminous flux having the second wavelength λ2 by a dichroic mirror 45. Then, a first light-receiving section 41 receives the scattered light having the first wavelength λ1, which has been received by the light-receiving optical system 40, and transforms it into the first light reception signal. A second light-receiving section 42 receives the scattered light having the second wavelength λ2, which is received by the light-receiving optical system 40, and transforms it into the second light reception signal. It is preferable that the first light-receiving section 41 and the second light-receiving section 42 be a light-receiving device such as a photo-multiplier.

The displacement section 60 will be described. The displacement section 60 consists of a rotating displacement section 61 that displaces the film-coated inspection subject 2 in a rotating manner, and a linear displacement section 62 that linearly displaces the film-coated inspection subject 2. The linear displacement section 62 is moved by a predetermined ratio of the width of luminous flux at one rotation displacement of the rotating displacement section 61, and thus the irradiation light from the irradiation optical system 20 spirally scans the film-coated inspection subject 2 from edge to edge.

The present invention is not limited to the above-described scanning method, but the irradiation luminous flux may perform linear scanning by a polygon mirror or the like instead of the rotating displacement.

In the embodiment of FIGS. 1 to 3, the rotating displacement section 61 consists of a rotation motor that rotates a rotating table, and the linear displacement section 62 consists of a sliding movement section that linearly moves the rotation motor. The sliding movement section, with its movement, displaces the rotation motor such that the irradiation position of the irradiation luminous fluxes 11, 12 from the irradiation optical system 20 passes the center of the inspection subject 2 and crosses in a diameter direction.

FIG. 3 is the block diagram of the surface inspection apparatus shown in FIG. 1.

The first light reception signal from the first light-receiving section and the second light reception signal from the second light-receiving section are transformed into digital signals by a first A/D converter 51 and a second A/D converter 52 respectively, and then are sent to a control arithmetic section 120 to perform a predetermined arithmetic processing. The control arithmetic section 120 performs a predetermined arithmetic processing (described later), where it displays an inspection result and a calculation result on a display section of an interface means 130, stores them in a storage section 140, and reads out the stored content.

The inspection data (data regarding wavelength of inspection light, polarization, incident angle and the like) of the inspection apparatus are associated with various kinds of parameters (such as film thickness and refraction index) regarding the film so as to have the optimum correlation, and previously stored in the storage section 140.

The control arithmetic section 120 consists of the arithmetic means and control means.

The arithmetic means automatically calculates (selects) the values for the proper optical inspection conditions based on the film parameters input to the apparatus in performing measurement according to the correlation between the inspection data and film parameters stored in the storage section 140.

The control means controls the optical inspection conditions of the apparatus, which are the wavelength of inspection light, polarization, incident angle and the like, for example, by the data from the arithmetic means.

Moreover, the control arithmetic section 120 controls the rotation motor of the rotating displacement section 61, the sliding movement section of the linear displacement section 62, or the sensitivity of the first light-receiving section 41 and second light-receiving section 42.

The interface means 130 displays information such as the inspection result and calculation result (graph) for the operator and enables the operator to enter desired data and parameters. The interface means 130 includes the display means and setting means (monitor, keyboard, mouse, touch panel and the like, for example).

Although not shown, the sensor means is provided to detect (monitor) the wavelength of the inspection light, polarization and incident angle.

Generally, the transmissive film and the foreign particle detection sensitivity approximate the relationship between the reflectance and the film thickness. In other words, the higher the reflectance is, the higher the detection sensitivity becomes.

The refraction index is basically used as the parameter regarding the film on the wafer, and the reflectance can be found by a general relational expression from the refraction index, film thickness and material.

Figure 4:
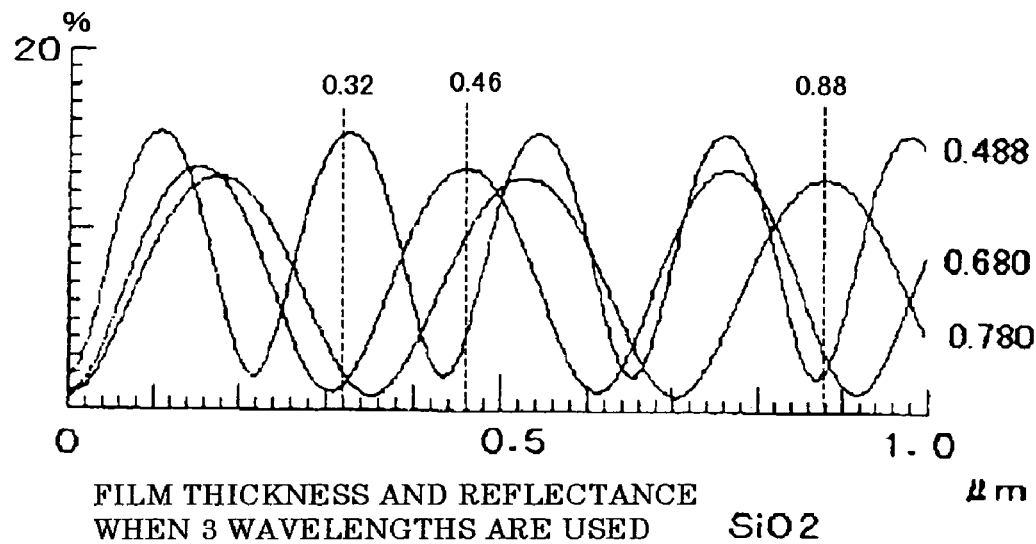
FIG. 4 is a graph showing the relationship between the film thickness and reflectance of the transmissive film when luminous fluxes having 3 wavelengths are irradiated on the film-coated wafer.

FIG. 4 is the graph showing the relationship between the film thickness and the reflectance of the transmissive film when luminous fluxes having 3 wavelengths of 0.488 μm, 0.680 μm and 0.780 μm have been irradiated on the transmissive film coated wafer.

It is understood that periods of peaks having large reflectance and valleys having small reflectance are different depending on the wavelength. For this reason, when a few luminous fluxes having different wavelengths are selectively combined and are made incident coaxially and simultaneously to perform inspection, number of places having sensitivity significantly different from other places are reduced comparing to the case where a luminous flux having one wavelength is made incident to perform inspection. In short, the reflectance is maintained at a constant level. Specifically, a case is assumed where the film-coated wafers provided with the transmissive films having the film thickness of 0.32 μm, 0.46 μm and 0.88 μm are mixed in a line. In this case, light having the wavelength of 0.488 μm is selected when measuring the film-coated wafer provided with the transmissive film of 0.32 μm, light having the wavelength of 0.680 μm is selected when measuring the film-coated wafer provided with the transmissive film of 0.46 μm, and light having the wavelength of 0.780 μm is selected when measuring the film-coated wafer provided with the transmissive film of 0.88 μm, and thus measurement can be performed with appropriate sensitivity in measuring a wafer of any film thickness.

Table 1 shows compatibility between the film thickness and the wavelength selected. In Table 1, the symbols ◎, ○ and - respectively show optimum, good, and unfavorable.

TABLE 1

| Film Thickness (μm) | Wavelength (μm) | | |
|---|---|---|---|
| | 0.488 | 0.680 | 0.780 |
| 0.32 | ◎ | — | — |
| 0.46 | — | ◎ | ○ |
| 0.88 | — | — | ◎ |

When the luminous fluxes having such wavelengths are selected, sensitivity is prevented from becoming unstable due to the changes of the film thickness of the transmissive films, the sensitivity is stabilized, and thus the optimum inspection conditions are obtained.

The first light reception signal received by the light-receiving section 41 is transformed from an analog signal into a digital signal by the first A/D converter 51. The second light reception signal received by the light-receiving section 42 is transformed from the analog signal into the digital signal by the second A/D converter 52.

The first light reception signal and second light reception signal, which have been transformed into the digital signals, are sent to the control arithmetic section 120, and the control arithmetic section 120 selects the optimum optical inspection conditions for each inspection position on the film-coated wafer surface.

Regarding the control of optical inspection conditions in the apparatus by the control means, light sources 110, 210, a lens unit 50, and the angle of a mirror 123 respectively control the wavelength, polarization and incident angle.

The present invention is not limited to the above-described embodiment.

The luminous fluxes that are made incident on the surface of the film-coated wafer may be three ore more luminous fluxes having different wavelengths from each other.

Figure 5:
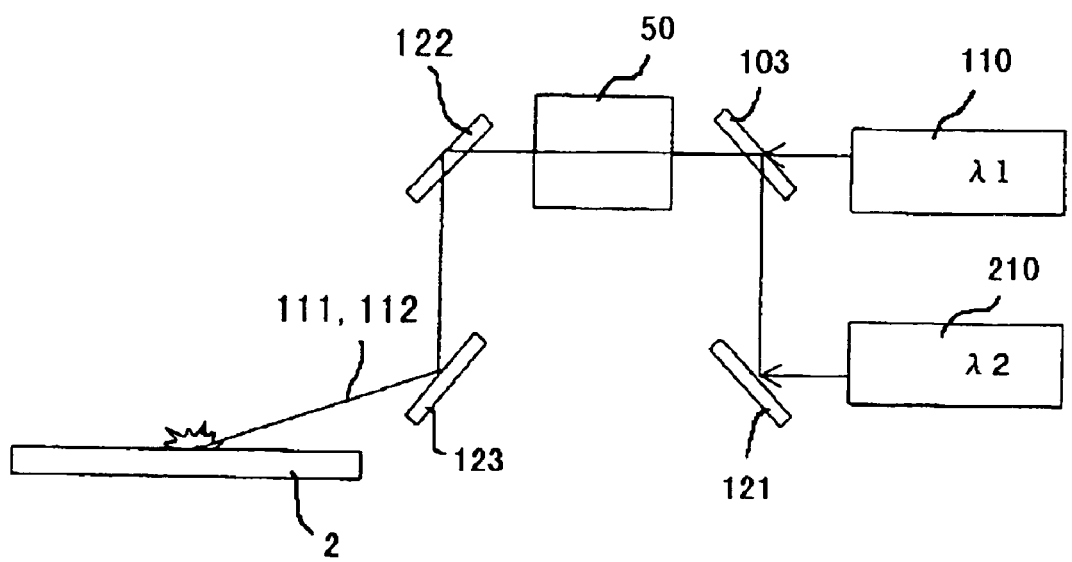
FIG. 5 is a block diagram of a system having a plurality of light sources that emit luminous fluxes of different wavelengths.

Further, as shown in FIG. 5, a plurality of light source sections 110, 210 that emit luminous fluxes having different wavelengths may be used as the light source section. In this case, the light source sections 110, 210 are severally capable of controlling ON/OFF. A luminous flux 111 having the wavelength λ1 emitted from the light source section 110 passes a half mirror 103. A luminous flux 112 having the wavelength λ2 emitted from the light source section 210 is reflected by a mirror 121. The luminous flux 112 having the wavelength λ2 reflected by the mirror 121 is reflected by the half mirror 103. The luminous flux 111 having the wavelength λ1 and luminous flux 112 having the wavelength λ2 pass the lens unit 50. The lens unit 50 has a beam shaping function and a polarization selecting function. The luminous flux 111 having the wavelength λ1 having passed the lens unit 50 is reflected by a mirror 122 and the mirror 123, and irradiated on the film-coated inspection subject 2. The luminous flux 112 having the wavelength λ2 having passed the lens unit 50 is reflected by the mirror 122 and mirror 123, and irradiated on the film-coated inspection subject 2.

Figure 6:
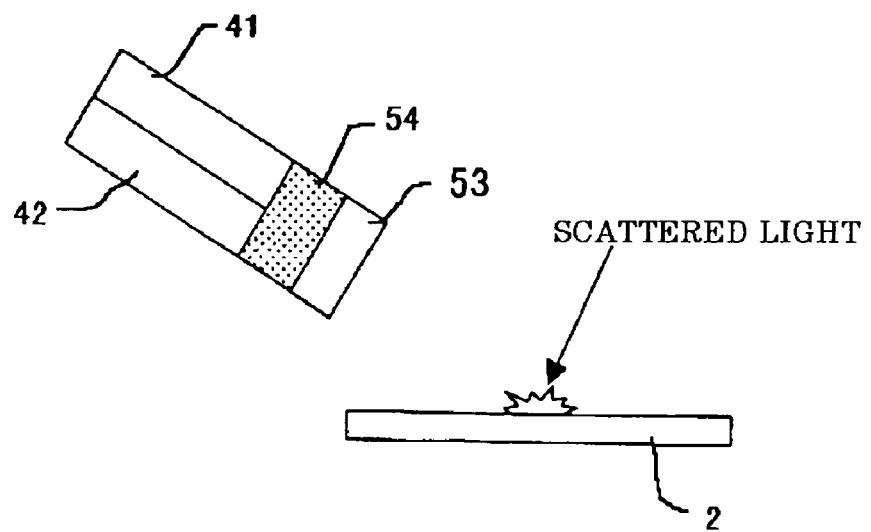
FIG. 6 is a block diagram of a detection system used in the system shown in FIG. 5.

As shown in FIG. 6, the detection system made up of a lens 53, a wavelength discriminating device 54 and the light-receiving devices 41, 42 detects the scattered light after the luminous fluxes 111, 112 have been irradiated on the film-coated inspection subject 2.

Furthermore, a plurality of luminous fluxes irradiated in the present invention may be irradiated not only from a same direction but also irradiated from different directions by a same irradiation angle.

Moreover, it is also possible that a plurality of luminous fluxes irradiated are made incident in different angles from each other. In this case, the light-receiving optical system receives the scattered light for every luminous flux having a different wavelength, and is capable of detecting the inspection subject by the irradiation luminous flux having an arbitrary incident angle.

Further, the luminous fluxes used in the present invention may be luminous fluxes having different polarization component from each other instead of a plurality of luminous fluxes having different wavelengths from each other. In performing the surface inspection of the film-coated inspection subject by using the luminous fluxes having different polarization component from each other, the detection system uses the polarizing plate.

Figure 7:
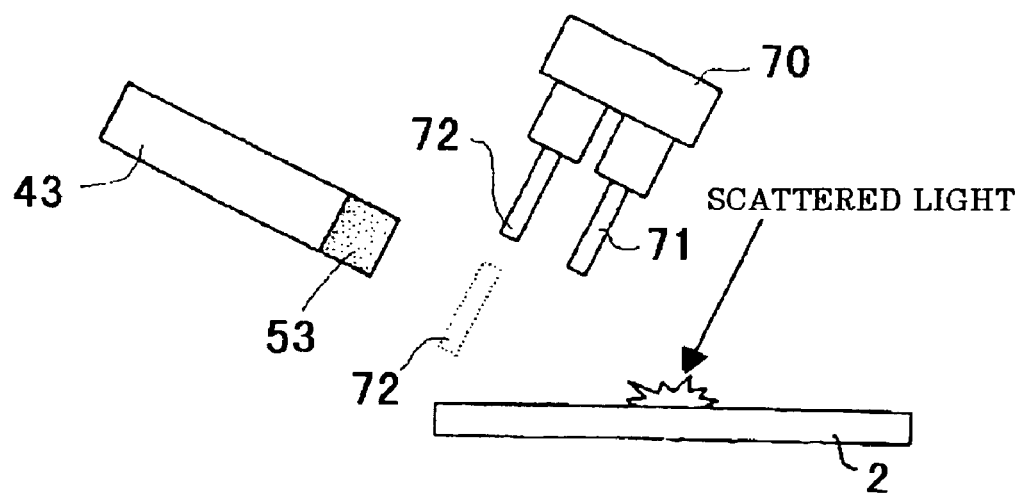
FIG. 7 is a view showing a detection system using a polarizing plate.

FIG. 7 is the view showing an example of the detection system using the polarizing plate.

The detection system using the polarizing plate consists of cylinder mechanism 70, polarizing plates 71, 72, the lens 53, and a light-receiving device 43. The cylinder mechanism 70 moves the polarizing plates 71, 72.

In the case of detection using the polarizing plates, the light-receiving device 43 receives the scattered light, which is generated after the luminous fluxes 111, 112 have been irradiated on the film-coated inspection subject 2, via the polarizing plate 72 and the lens 53. Then, the light reception signal is formed for each polarization component.

Figure 8:
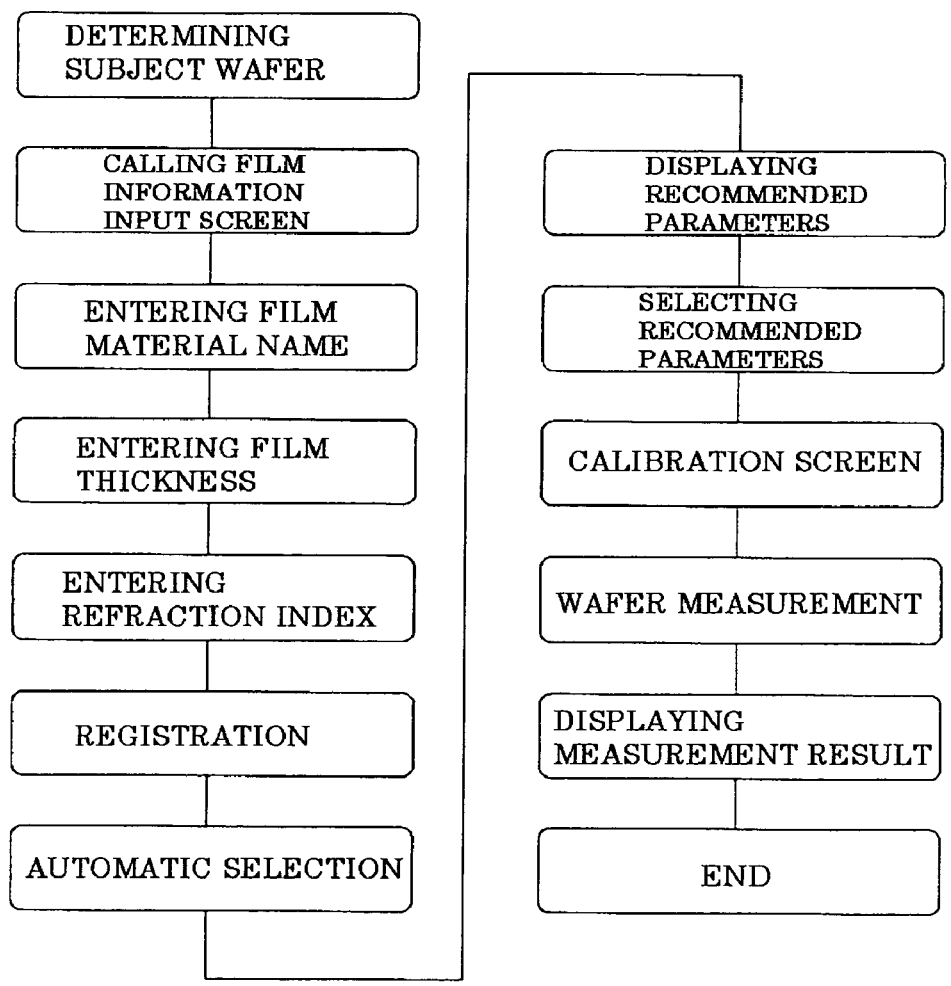
FIG. 8 is a flowchart of selecting the film parameters according to one embodiment of the present invention.

FIG. 8 shows an example of the flow of film parameter selection.

Several combinations of recommended parameters are presented in order from higher priority. The operator selects the optimum combination, or selects other recommended parameters again if he/she is not satisfied with a measurement result, and performs measurement one more time.

When the operator enters the film parameters, the control arithmetic section 120 creates a reflectance graph, and the operator decides the combination of the recommended value parameters based on the information to display them on the interface means 130.

Rules regarding recommendation are separately described, which is called in a program or made to operate as a program embedment.

Figure 9:
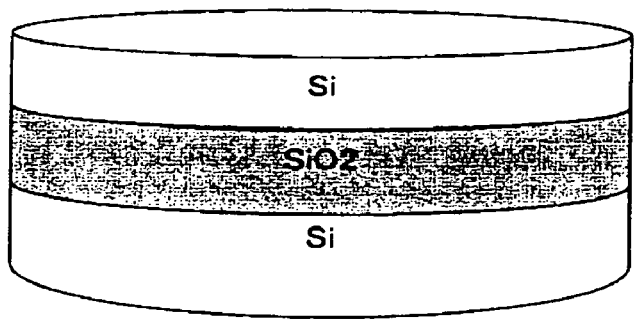
FIG. 9 shows an example of an SOI wafer.

FIG. 9 shows an example of the SOI wafer.

In the SOI wafer structure shown in FIG. 9, the thickness of a surface Si layer and the thickness of an inner $SiO_2$ layer are different for every user, which shows a complicated reflectance.

Figure 10:
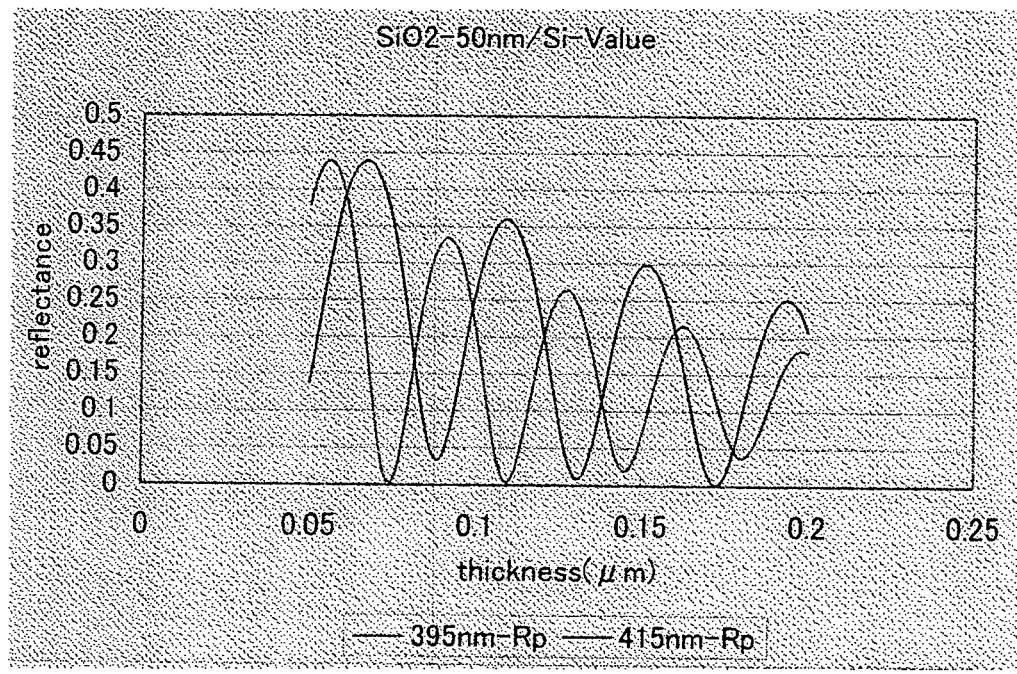
FIG. 10 is a graph showing reflectance variation in the case of different thickness of Si layers when an $SiO_2$ layer is fixed to 50 nm.

FIG. 10 shows the reflectance variation in the case where the thickness of the Si layer is different when the $SiO_2$ layer in the SOI wafer structure of FIG. 9 is fixed to 50 nm.

Example 1 of input items of such an SOI wafer is described as follows.

First film thickness: 110 nm
Film type: Si
First refraction index: -
Second film thickness: 50 nm
Second film type: $SiO_2$
Second refraction index: -

Note that there is a case of no input of the refraction index because the wavelengths used in the apparatus are known.

An alarm or an error is separately displayed in the case of a material that has not been registered.

A material used for the first time needs to be entered for each wavelength used by the apparatus.

Further, another example 2 is shown as follows.

First film thickness: 110 nm
Film type: Si
First refraction index-1: 5.0
First refraction index-2: 5.63
Second film thickness: 50 nm
Second film type: $SiO_2$
Second refraction index-1: 1.480
Second refraction index-2: 1.486

In the above-described examples 1 and 2, example 1 is for the case of 415 nm and example 2 is for the case of 395 nm. In the both examples 1 and 2, the control arithmetic section 120 performs calculation based on the film parameters entered by the operator after the items are entered, and the optimum wavelength and the polarization are displayed on the interface means 130.

Figure 11:
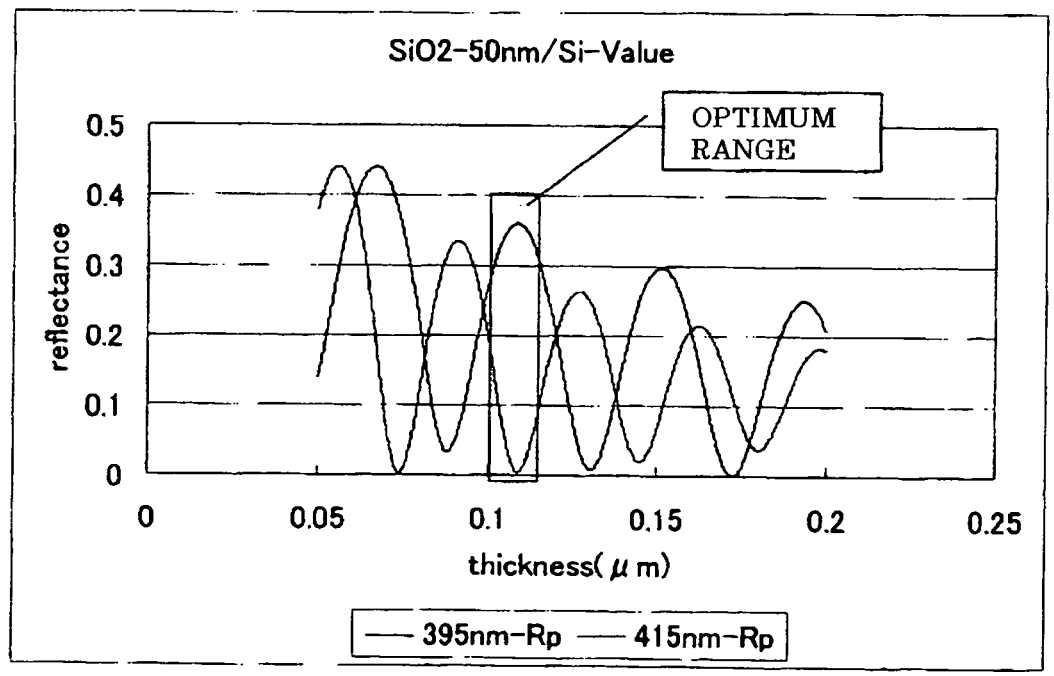
FIG. 11 shows an optimum range by a rectangular frame, which is calculated from the graph in FIG. 10.

FIG. 11 is an example of the graph of the reflectance, which is calculated based on the film parameters entered by the operator in this manner.

In FIG. 11, the rectangular frame is selected as the optimum range. In the case of the above-described Si-110 nm, P-polarized light is automatically selected as the first candidate at 415 nm. The second candidate is P-polarized light at 395 nm.

Note that, in the case of FIG. 11, determination is made based on an empirical rule that P-polarized light is advantageous because the surface is the Si layer.

A file that describes the empirical rule may be used, or it may be embedded in the program.

After selecting the first candidate, the apparatus operates the polarizing plate for LD use to create P-polarized light, drives the optical system such that the wavelength of 415 nm is made incident by a predetermined incident angle, and ends preparation of a hardware system.

According to the present invention, by setting (input or selection) each kind of parameters regarding the film formed on a wafer to be inspected, the optimum optical inspection conditions are automatically set, and thus measurement can be performed.

In the surface inspection apparatus capable of switching or mixing two or more kinds of wavelength by a same incident angle, the settings of optimum optical inspection conditions can be automated. As a result, even the non-experienced operator can perform highly accurate settings easily. Foreign particles in a semiconductor factory can be efficiently and optimally controlled, which can contribute to the improvement of yield.

Since the SOI wafer has different film thickness for each individual application, the optimum conditions have to be found for each application requiring the user to have an additional calibration operation or higher knowledge of optics, which becomes a difficult operation. However, according to the present invention, advance in automation can be achieved. It is possible to easily set the optimum inspection conditions even in the case of the wafer such as the SOI wafer having the different film thickness for each individual application, the case where the operator does not fully understand the complicated operation of apparatus, or is not skillful in the operation of apparatus. By entering necessary film parameters, the apparatus automatically derives the optimum conditions, so that the user uses the apparatus very simply and can perform intended measurement.

Furthermore, when the apparatus is designed to show necessary items regarding condition settings to the operator, he/she can easily perform the condition settings without fail.

What is claimed is:

1. A surface inspection method for inspecting a plurality of inspection subjects having films coated thereon, comprising the steps of:
    storing inspection data regarding an inspection apparatus and film parameters regarding the films coated on the inspection subjects, by associating with each other, so as to obtain predetermined inspection conditions;
    wherein the inspection conditions are the wavelength of a laser, an incident angle, and a polarization, and
    automatically setting a wavelength of a laser, an incident angle, and a polarization as the predetermined inspection conditions for the inspection apparatus by selecting the film parameters of the inspection subjects to be measured in the inspection apparatus by an operator, when performing each measurement,
    wherein the inspection subjects to be measured are in a manufacturing line,
    wherein the films coated on the inspection subjects to be measured vary in thickness from one inspection subject to another, and two or more kinds of laser which emit luminance flux having different wavelengths to each other are switched or mixed to make a laser incident on the film-coated inspection subjects at a same incident angle.

2. The surface inspection method according to claim 1, wherein the film parameters set by the operator include a film thickness and a refraction index.

3. The surface inspection method according to claim 1, wherein only the film thickness of the inspection subject to be measured is selected, when performing each measurement.

4. A surface inspection apparatus for inspecting a plurality of inspection subjects, comprising:
    an inspection data storage device that is configured to store inspection data regarding an inspection apparatus and film parameters regarding films coated on the inspection subjects, by associating with each other, so as to obtain predetermined inspection conditions;

a setting device that is configured to set, by an operator, the film parameters of the inspection subjects, when performing each measurement;

an arithmetic device that is configured to automatically calculate the predetermined inspection conditions on a basis of the film parameters set by the setting device; and a controller that is configured to control the inspection apparatus on a basis of the predetermined inspection conditions calculated by the arithmetic device, wherein the films coated on the inspection subjects vary in thickness from one inspection subject to another, wherein the inspection subjects to be measured are in a manufacturing line, wherein the surface inspection apparatus is configured to provide two or more kinds of laser which emit luminance flux having different wavelengths to each other, wherein the surface inspection apparatus is configured to switch or mix the two or more kinds of laser to make a laser incident on the film-coated inspection subjects at a same incident angle, wherein the inspection conditions are the wavelength of a laser, an incident angle, and a polarization.

5. The surface inspection apparatus according to claim 4, wherein the film parameters set by the setting device include a film thickness and a refraction index.

6. The surface inspection apparatus according to claim 4, wherein only the film thickness of the inspection subject to be measured is selected, when performing each measurement.

7. A method of inspecting a surface of film-coated inspection subjects, comprising the steps of:

providing film parameters for a film coated on an inspection subject and storing the film parameters in an inspection apparatus;

determining inspection data for the film by performing a light inspection of the inspection subject and storing the inspection data in the inspection apparatus;

automatically selecting optimum inspection conditions, wherein the inspection conditions are determined from a correlation of the inspection data to the stored film parameters, wherein the inspection conditions include a wavelength of the light, an incident angle, and a polarization; and performing light inspection of film-coated inspection subjects on a basis of the selected optimum inspection conditions, wherein light inspection is performed using two or more different wavelengths that are switched or mixed with one another and are incident on the film-coated inspection subjects at a same incident angle;

wherein films of the inspection subjects vary in thickness from one inspection subject to another;

wherein the inspection subjects to be measured are in a manufacturing line.

8. The method according to claim 7, wherein the film parameters comprise film thickness and a film refraction index.

9. The method according to claim 7, wherein the film parameters consist of film thickness.

10. The method according to claim 7, wherein the film parameters are provided by an operator.

11. The method according to claim 7, wherein inspection conditions comprise a laser wavelength, the incident angle, and the polarization.

* * * * *